US008100873B2

(12) United States Patent
Jaeb et al.

(10) Patent No.: US 8,100,873 B2
(45) Date of Patent: Jan. 24, 2012

(54) SYSTEM AND METHOD FOR COLLECTING EXUDATES

(75) Inventors: Jonathan Paul Jaeb, Boerne, TX (US); Randall Paul Kelch, San Antonio, TX (US); Christopher Brian Locke, Bournemouth (GB); James Luckemeyer, San Antonio, TX (US); Terrie Lea McDaniel, Helotes, TX (US); Bruce Phillips, San Antonio, TX (US); Timothy Mark Robinson, Basingstoke (GB); Abhay Jaswal, San Antonio, TX (US); Kevin Higley, San Antonio, TX (US); Tyler Simmons, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 512 days.

(21) Appl. No.: 12/395,113

(22) Filed: Feb. 27, 2009

(65) Prior Publication Data
US 2009/0221990 A1 Sep. 3, 2009

Related U.S. Application Data

(60) Provisional application No. 61/032,804, filed on Feb. 29, 2008.

(51) Int. Cl.
*A61M 1/00* (2006.01)
(52) U.S. Cl. ........ 604/319; 604/317; 604/318; 604/540; 137/216; 137/254; 137/262; 137/395; 138/37; 138/42; 141/44; 141/286; 239/461; 239/462; 239/483; 239/498; 239/499; 239/504; 239/505; 239/507; 239/509; 239/512; 239/518; 239/521; 239/522; 239/523; 239/524
(58) Field of Classification Search .................. 604/319, 604/540, 317, 318; 137/216, 254, 262, 395; 138/37, 42; 141/44, 286; 239/461, 462, 483, 498–499, 504–505, 507, 509, 512, 518, 521–524
See application file for complete search history.

(56) References Cited

U.S. PATENT DOCUMENTS 1,355,846 A 10/1920 Rannells
(Continued)

FOREIGN PATENT DOCUMENTS

AU 550575 A1 8/1982
(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (copy and certified translation).

(Continued)

*Primary Examiner* — Tatyana Zalukaeva
*Assistant Examiner* — Ginger T Chapman

(57) ABSTRACT

A reduced pressure treatment system includes a porous pad positioned at a tissue site and a canister having a collection chamber, an inlet, and an outlet. The inlet is fluidly connected to the porous pad. A reduced pressure source is fluidly connected to the outlet of the canister to such that fluid from the tissue site may be drawn into the collection chamber. A hydrophobic filter is positioned adjacent the outlet to prevent liquid from exiting the collection chamber through the outlet. A baffle is positioned within the canister to create a tortuous path between the inlet and the outlet to prevent premature blocking of the hydrophobic filter.

32 Claims, 7 Drawing Sheets

U.S. PATENT DOCUMENTS

| | | | |
|---|---|---|---|
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,863,634 A * | 2/1975 | Reynolds et al. | 604/318 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,317,525 A | 3/1982 | Schuessler et al. | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,444,548 A * | 4/1984 | Andersen et al. | 417/63 |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,955,874 A * | 9/1990 | Farrar et al. | 604/319 |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,087,250 A * | 2/1992 | Lichte et al. | 604/321 |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,722,964 A * | 3/1998 | Herweck et al. | 604/317 |
| 6,071,267 A | 6/2000 | Zamierowski | |
| 6,135,116 A | 10/2000 | Vogel et al. | |
| 6,210,383 B1 * | 4/2001 | Want et al. | 604/318 |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,063,688 B2 * | 6/2006 | Say | 604/319 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0148465 A1 | 10/2002 | Sealfon | |
| 2002/0161317 A1 | 10/2002 | Risk et al. | |

FOREIGN PATENT DOCUMENTS

| | | |
|---|---|---|
| AU | 745271 | 4/1999 |
| AU | 755496 | 2/2002 |
| CA | 2005436 | 6/1990 |
| CA | 2488867 A1 | 6/2006 |
| DE | 26 40 413 A1 | 3/1978 |
| DE | 92 03 039 U1 | 5/1992 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0 777 504 | 6/1997 |
| EP | 1 184 043 | 3/2002 |
| EP | 1018967 B1 | 8/2004 |
| EP | 1 837 045 | 9/2007 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO-2007/143677 A2 | 12/2007 |
| WO | WO-2009/007702 A | 1/2009 |
| WO | WO 2009/007702 A | 1/2009 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164 (copy and certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

International Search Report and Written Opinion date mailed Sep. 4, 2009; PCT International Application No. PCT/US2009/035567.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

International Search Report and Written Opinion date mailed Dec. 14, 2009 for PCT International Application No. PCT/US2009/035567.

\* cited by examiner

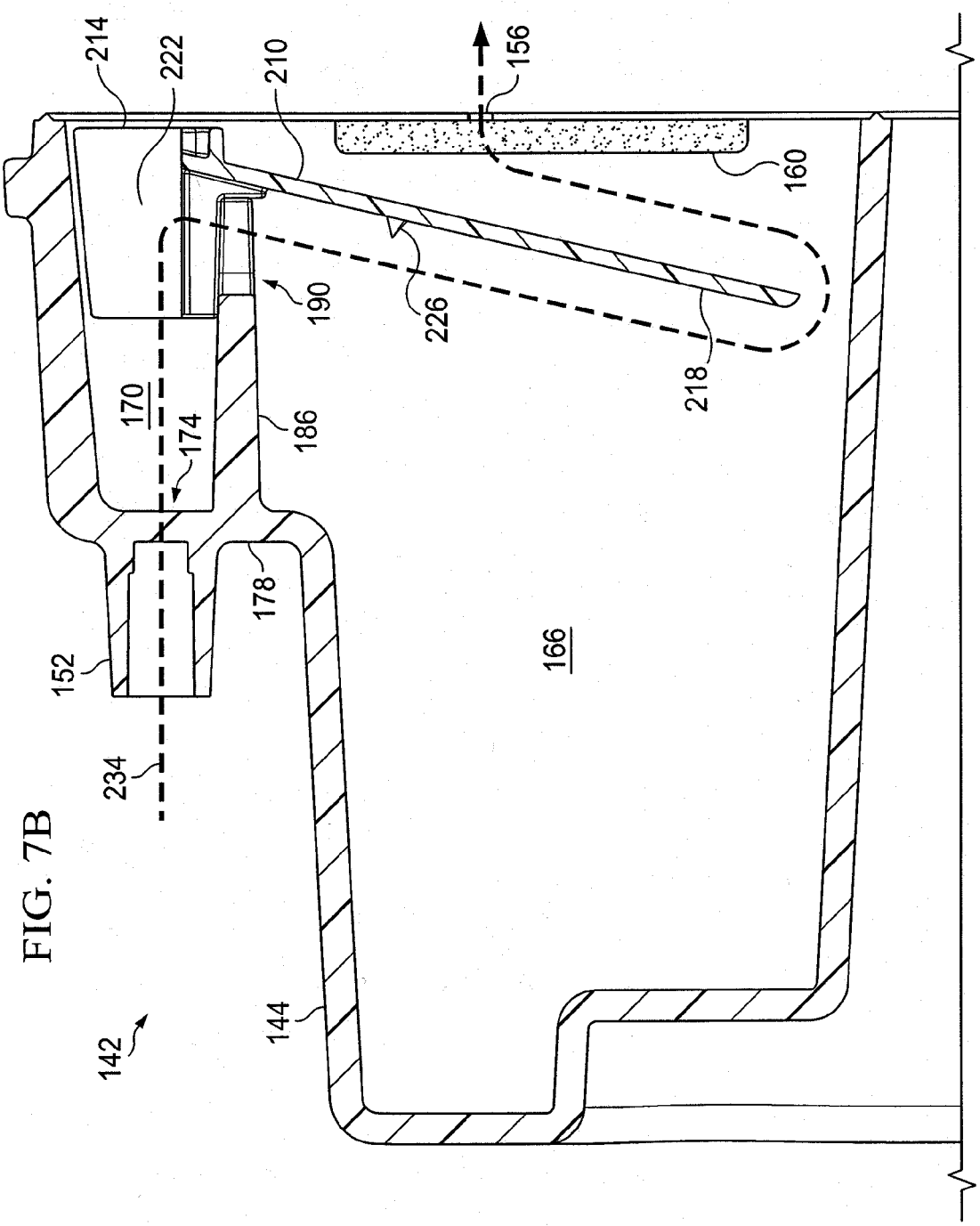

_US 8,100,873 B2_

SYSTEM AND METHOD FOR COLLECTING EXUDATES

CROSS-REFERENCE TO RELATED APPLICATIONS

This application claims the benefit of U.S. Provisional Application No. 61/032,804 filed Feb. 29, 2008, which is hereby incorporated by reference.

BACKGROUND OF THE INVENTION

1. Field of the Invention

The present invention relates generally to tissue treatment systems and in particular to systems and methods for collecting exudates.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment.

Fluids or exudates are generally collected in a canister for disposal or analysis. Such collection canisters should separate fluids from air in the exudate stream to retain the fluids in the canister while permitting the excess air to be expelled. Numerous approaches to this requirement are known in the art, with a hydrophobic filter being the most common solution. In practice, many exudate canisters are a disposable component, and low cost and ease of manufacture are important considerations. Complex structures and unnecessary components in the canisters are undesirable. The hydrophobic filters are optimized to maximize dry air flow while maintaining acceptable fluid blockage, permitting small size and minimizing cost.

SUMMARY

The problems presented by existing collection canisters are solved by the systems and methods of the illustrative embodiments described herein. In one illustrative embodiment, a reduced pressure treatment system is provided. The reduced pressure treatment system includes a porous pad positioned at a tissue site and a canister having a collection chamber, an inlet, and an outlet. The inlet is fluidly connected to the porous pad. A reduced pressure source is fluidly connected to the outlet of the canister to deliver a reduced pressure to the collection chamber and the tissue site such that fluid from the tissue site is drawn into the collection chamber. A liquid-air separator is associated with the outlet to prevent liquid from exiting the collection chamber through the outlet. A baffle is positioned within the canister to deflect liquid entering the canister from prematurely blocking the liquid-air separator.

In another illustrative embodiment, a collection canister for use with a reduced pressure treatment system is provided. The canister includes a collection chamber, an inlet adapted to be fluidly connected to a tissue site, and an outlet adapted to be fluidly connected to a reduced pressure source. A liquid-air separator is positioned adjacent the outlet, and a baffle is positioned within the canister to deflect liquid entering the canister from prematurely blocking the liquid-air separator.

In still another illustrative embodiment, a collection canister is provided for use with a reduced pressure treatment system. The canister includes a collection chamber and an entry chamber positioned above the collection chamber. The entry chamber includes an open end and a closed end defined by an entry wall. The entry chamber further includes a floor separating the entry chamber from the collection chamber, the floor having an aperture allowing communication between the entry chamber and the collection chamber. An inlet is disposed in the entry wall of the entry chamber, and the inlet is adapted to be fluidly connected to a tissue site. An outlet is in communication with the collection chamber and is adapted to be fluidly connected to a reduced pressure source. A hydrophobic filter is positioned adjacent the outlet to prevent liquid from exiting the collection chamber through the outlet. A baffle having a base and a deflector plate is provided, and the base is removably positioned within the entry chamber through the opening of the entry chamber. The deflector plate of the baffle deflects liquid entering the entry chamber through the inlet from prematurely blocking the hydrophobic filter.

In yet another illustrative embodiment, a collection canister for use with a reduced pressure treatment system is provided. The canister includes a collection chamber, an inlet adapted to be fluidly connected to a tissue site, an outlet adapted to be fluidly connected to a reduced pressure source, and a liquid-air separator positioned adjacent the outlet. A baffle is positioned within the canister to receive droplets or spray from bubbles bursting within the canister.

In another illustrative embodiment, a collection canister for use with a reduced pressure treatment system is provided. The canister includes a collection chamber and an entry chamber positioned above the collection chamber. The entry chamber has an open end and a closed end defined by an entry wall. The entry chamber further includes a floor separating the entry chamber from the collection chamber, the floor having an aperture allowing communication between the entry chamber and the collection chamber. An inlet is disposed in the entry wall of the entry chamber, and the inlet is adapted to be fluidly connected to a tissue site. An outlet is provided in communication with the collection chamber and is adapted to be fluidly connected to a reduced pressure source. A liquid-air separator is positioned adjacent the outlet to prevent liquid from exiting the collection chamber through the outlet, and a porous foam is positioned in the entry chamber to minimize bubble formation near the open end of the entry chamber.

In still another embodiment, a method for collecting exudate from a tissue site is provided. The method includes creating a reduced pressure within a collection canister to draw exudate from the tissue site to the collection canister. The collection canister includes an outlet and a liquid-air separator associated with the outlet. The method further includes minimizing deposition of protein from the exudate on the liquid-air separator.

Other objects, features, and advantages of the illustrative embodiments will become apparent with reference to the drawings and detailed description that follow.

BRIEF DESCRIPTION OF THE DRAWINGS

FIG. 7B depicts a partial, cross-sectional view of the canister and baffle of FIG. 2, the section taken along line 7B-7B of FIG. 7A.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Figure 1:
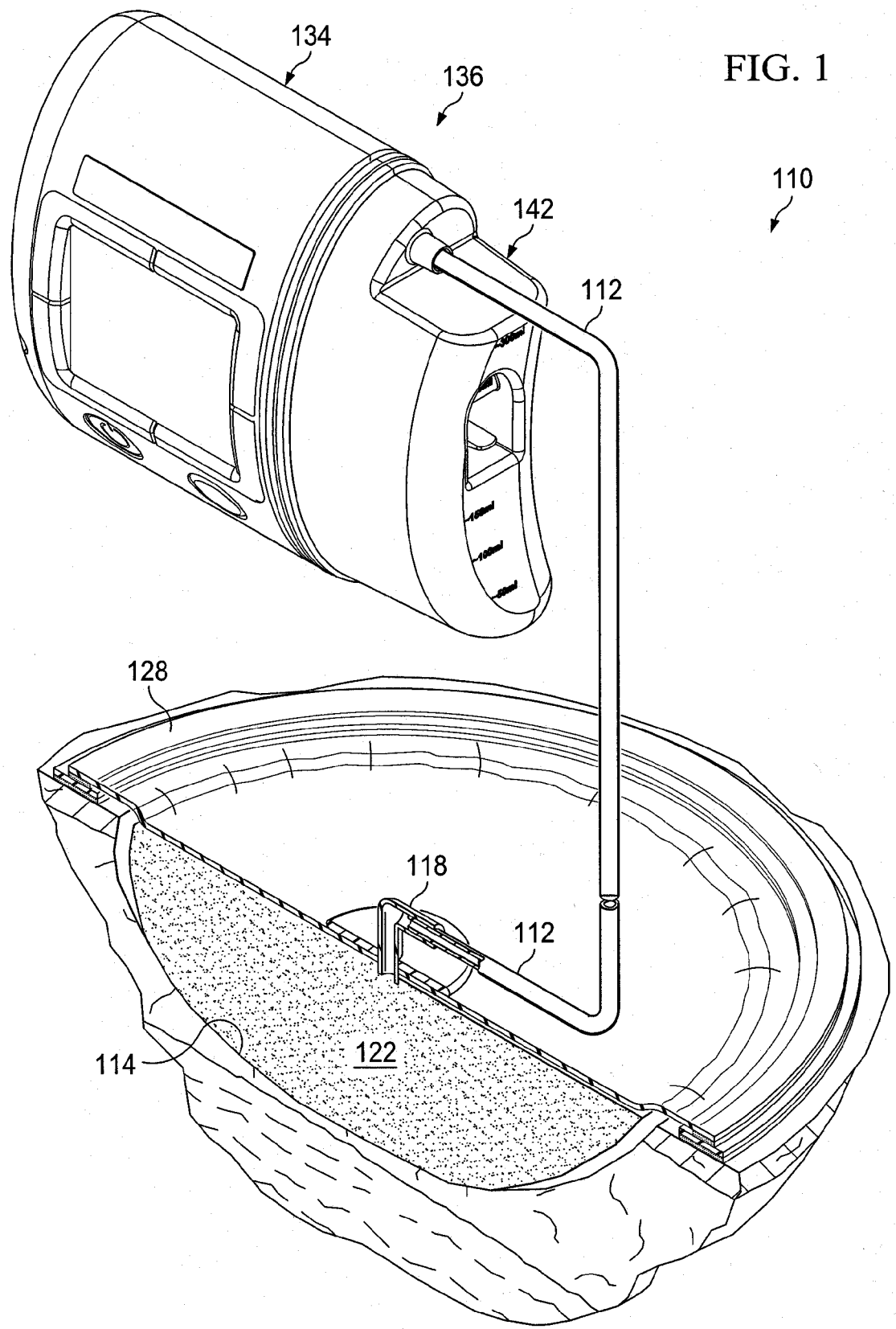
FIG. 1 illustrates a front perspective view of a reduced pressure treatment system having a collection canister and baffle according to an illustrative embodiment.

Referring to FIG. 1, a reduced pressure treatment system 110 according to an embodiment of the invention includes a conduit 112 in fluid communication with a tissue site 114 of a patient. The conduit 112 may fluidly communicate with the tissue site 114 through a tubing adapter 118 and a distribution manifold 122. The distribution manifold 122 may be any material, either bioabsorbable or non-bioabsorbable, that is capable of manifolding a reduced pressure to the tissue site 114. In one embodiment, the distribution manifold 122 may be an open-cell, reticulated polyurethane foam. A drape 128 may be placed over the distribution manifold 122 and sealed around a perimeter of the tissue site 114 to maintain reduced pressure at the tissue site 114.

The conduit 112 is fluidly connected to a reduced pressure source 134. In one implementation, the reduced pressure source 134 may be a reduced pressure or vacuum pump driven by a motor. In another embodiment, the reduced pressure source may be a manually-actuated pump such as a compressible bellows pump. In still another embodiment, the reduced pressure source 134 may be a wall suction port such as are available in hospitals and other medical facilities.

The reduced pressure source 134 may be housed within a reduced pressure treatment unit 136, which may also contain sensors, processing units, alarm indicators, memory, databases, software, display units, and user interfaces that further facilitate the application of reduced pressure treatment to the tissue site 114. In one example, a sensor (not shown) may be disposed at or near the reduced pressure source 134 to determine a source pressure generated by the reduced pressure source 134. The sensor may communicate with a processing unit that monitors and controls the reduced pressure that is delivered by the reduced pressure source 134. Delivery of reduced pressure to the tissue site encourages new tissue growth by maintaining drainage of exudate from the tissue site, increasing blood flow to tissues surrounding the tissue site, and by compressing the distribution manifold into the tissue site, thereby creating microstrain at the tissue site which stimulates new tissue growth.

Figure 2:
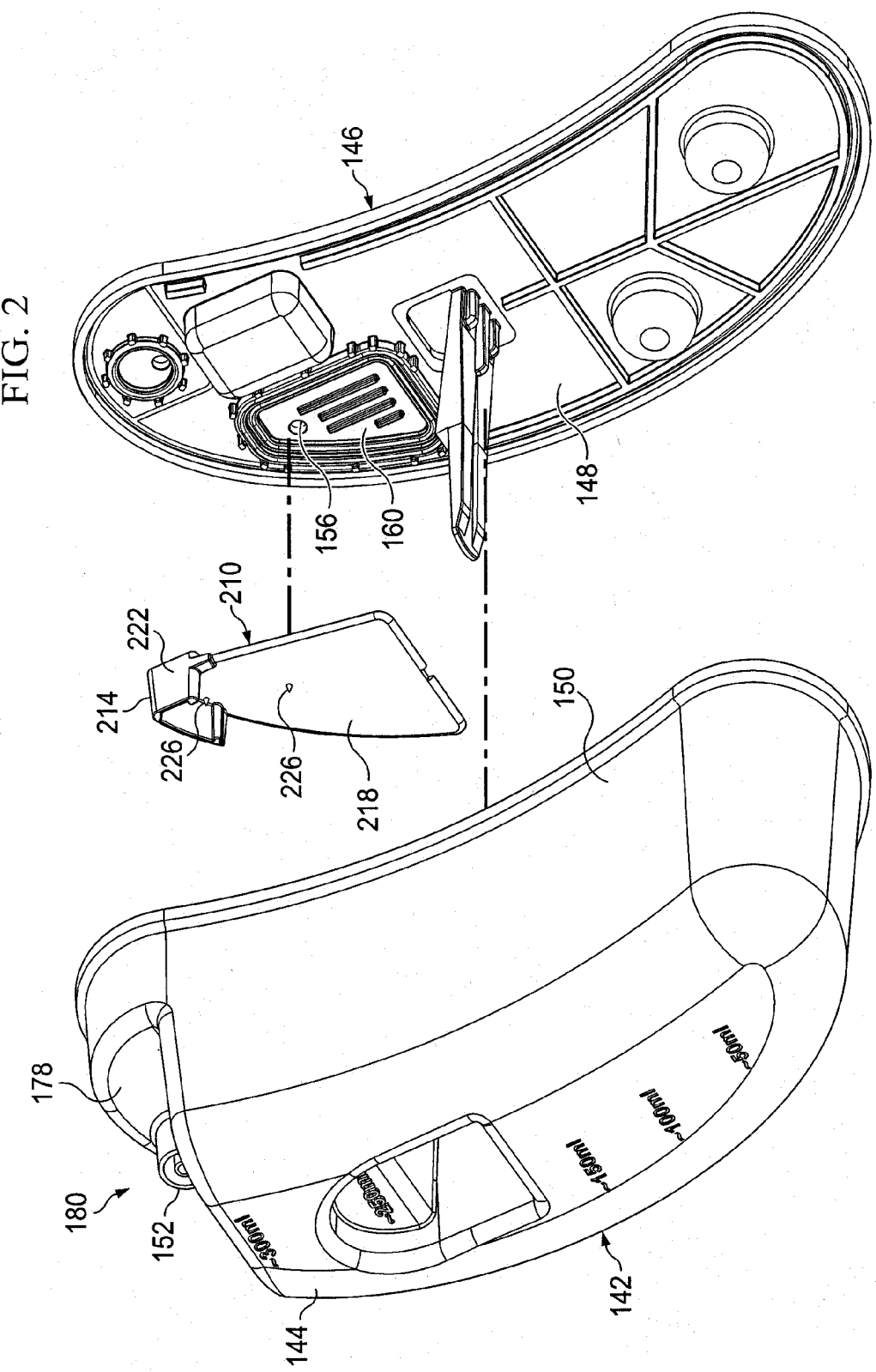
FIG. 2 depicts an exploded, front perspective view of the canister and baffle of FIG. 1.
Figure 3:
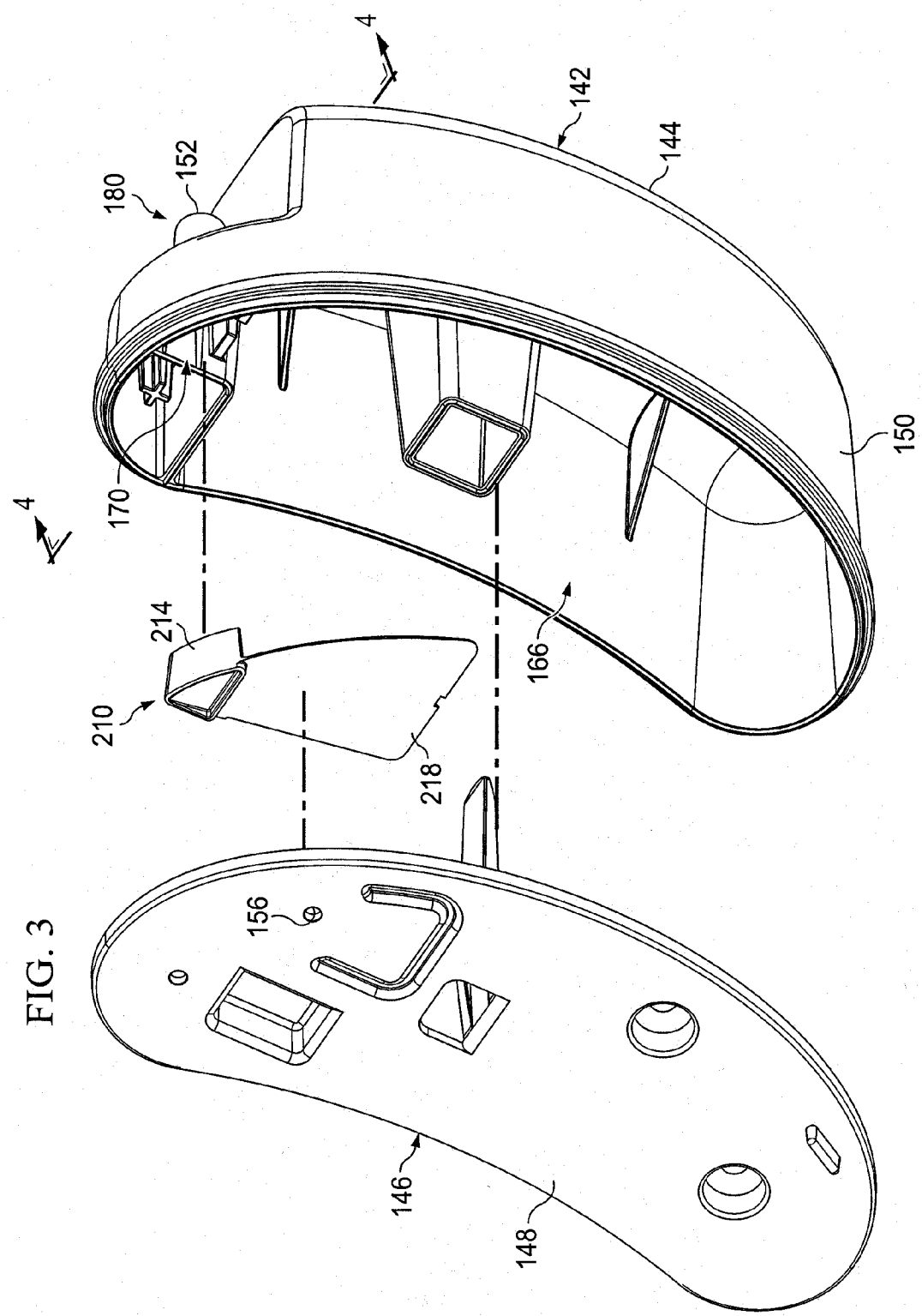
FIG. 3 illustrates an exploded, rear perspective view of the canister and baffle of FIG. 2.

Referring still to FIG. 1, but also to FIGS. 2 and 3, a canister 142 is fluidly connected between the reduced pressure source 134 and the tissue site 114 to collect exudate and other fluids drawn from the tissue site 114. In the embodiment shown in FIGS. 1-3, the canister includes a basin portion 144 and a lid portion 146. The lid portion 146 may be formed by an exit wall 148 that is substantially planar and is capable of mating with the basin portion 144. While the basin portion 144 is formed from a basin wall 150 that includes curved contours to create a crescent shape, the basin portion 144 and lid portion 146 may instead form a canister that is cylindrical, cubical, rectangular cubical, or any other shape. It should also be noted that the canister 142 may not include separate basin and lip portions, but rather may be formed from a substantially unitary housing.

The canister 142 includes an inlet 152 that is fluidly connected to the conduit 112, an outlet 156 that is fluidly connected to the reduced pressure source 134, and a liquid-air separator 160 operatively associated with the outlet 156 to prevent liquid from exiting the canister 142 through the outlet 156. The inlet 152 may be positioned on a wall 178 disposed in a recessed region 180 of the basin portion 144. In one embodiment, the outlet 156 is positioned in the exit wall 148, and the liquid-air separator 160 is positioned adjacent to the outlet 156 and secured to the exit wall 148. The outlet 156 allows fluid communication between the canister 142 and the reduced pressure source 134 such that a reduced pressure is capable of being maintained within the canister 142. This reduced pressure is capable of being transmitted to the tissue site through the inlet 152, the conduit 112, the tubing adapter 118, and the distribution manifold 122. The reduced pressure draws exudate and other fluids from the tissue site 114 into the canister 142. The liquid-air separator 160 prevents liquids that that are drawn into the canister 142 from exiting the canister 142 through the outlet 156 and contaminating the reduced pressure source 134.

In an illustrative embodiment, the liquid-air separator 160 may be a hydrophobic filter that prevents passage of liquids through the outlet 156. Alternatively, the liquid-air separator 160 may be a gravity-based barrier system, or a device that includes a hydrophilic surface to encourage condensation or other separation of liquid from a fluid stream when the fluid stream passes over the surface. Other examples of liquid-air separators 160 may include sintered metals, sintered nylons, or any other material or device that is capable of separating liquid from a fluid stream, or that is otherwise capable of preventing the passage of liquid while allowing the passage of gases.

Figure 4:
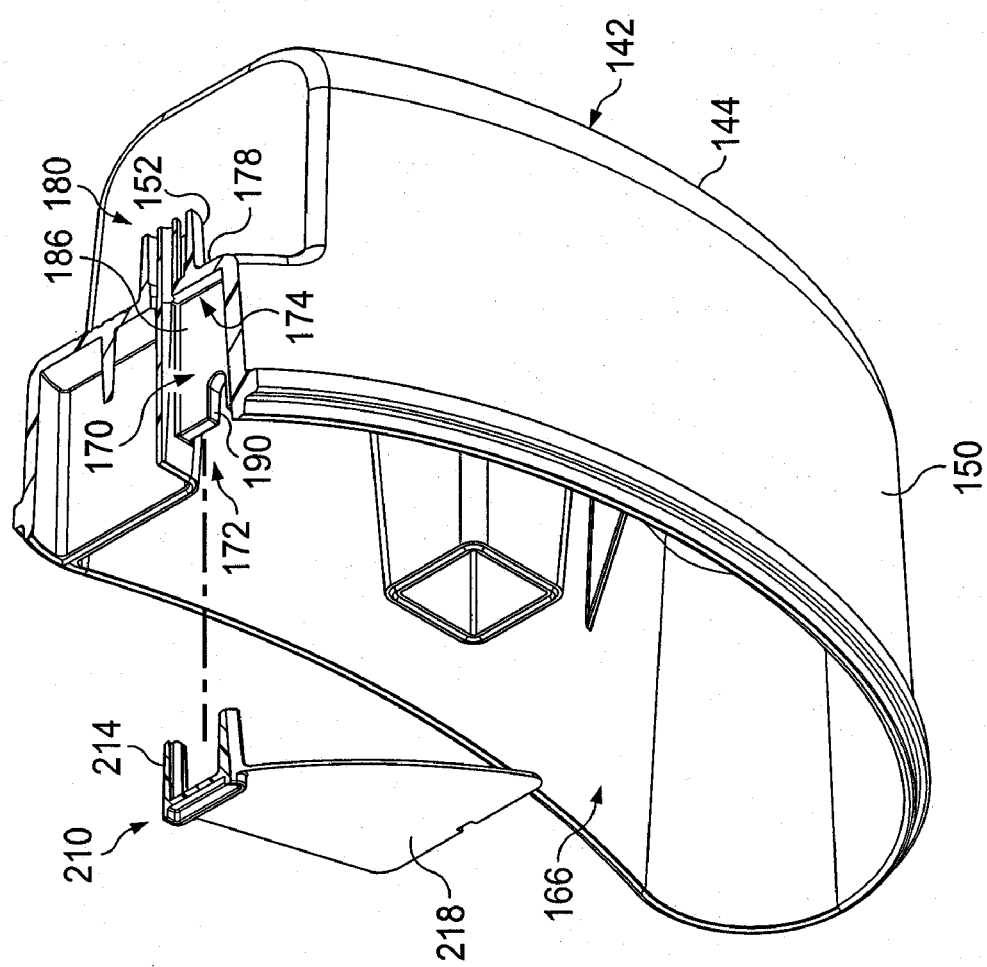
FIG. 4 depicts an exploded, partially-sectioned, rear perspective view of the canister and baffle of FIG. 2, the section taken along line 4-4 of FIG. 3.

Referring more specifically to FIGS. 2 and 3, and also to FIG. 4, in the illustrated embodiment, the canister 142 includes a collection chamber 166 that serves as the primary reservoir for collecting fluid within the canister 142. An entry chamber 170 is positioned above the collection chamber 166 and includes an open end 172 and a closed end 174. The closed end 174 of the entry chamber 166 is defined by the wall 178. The inlet 152 may be disposed in the wall 178 such that a primary lumen of the conduit 112 facilitates communication between the tissue site 114 and the entry chamber 170. The entry chamber 170 further includes a floor 186 that at least partially separates the entry chamber 170 from the collection chamber 166. Despite the presence of the floor 186, fluid communication will still be permitted between the entry chamber 170 and the collection chamber 166 through the open end 172 of the entry chamber 170 and through an aperture 190 positioned in the floor 186. The aperture 190, as illustrated in FIGS. 3 and 4, is a slot, but it should be noted that the aperture may be a hole, a channel, or any other aperture that improves communication between the entry chamber 170 and the collection chamber 166.

While the positions and shapes of the inlet 152, outlet 156, and entry chamber 170 have been described in detail above, the positioning, shape, and general configuration of the inlet 152, outlet 156, and entry chamber 170 may vary depending on the shape and configuration of the canister.

As described herein, the canister 142 is primarily used to collect exudate from the tissue site 114. Exudates from a small percentage of patients have unique chemical and physical properties. These properties promote bubble formation and foaming as fluid enters the canister, and the fluid may contain proteins that can adhere to many hydrophobic filter membranes. Under normal conditions, the protein film builds up gradually but is exacerbated when foaming is present. The presence of "exudate bubbles" maximizes the deposition phenomenon by atomizing minute droplets of protein-containing exudate when the bubbles pop. The small size of these droplets limits the liquid-shedding effects of the hydrophobic filter, and encourages their rapid evaporation. Upon evaporation, a protein residue is left behind on the surface where the droplets were located. When the residue accumulates on the surface of a hydrophobile filter, it impairs filter performance and airflow. This blockage can occur after collecting only a fraction of the canister's capacity, necessitating premature disposal of the canister and increasing operating costs. Under severe conditions, the filter can become completely occluded, which causes the system to fail to deliver the intended treatment. In the extreme case, the occlusion can lead to complete failure of the filter membrane, defeating the primary requirement of separating the fluid from the air, and permitting contamination of downstream components.

Referring to FIGS. 2-6, 7A, and 7B, a baffle 210 is provided to reduce the formation of protein bubbles, burst protein bubbles that have formed, and minimize the premature blocking of hydrophobic filters or other liquid-air separators 160 positioned in the canister 142. The baffle 210 includes a base 214 and a deflector plate 218, the base 214 having a shroud 222 that may be integrally attached to the deflector plate 218. In another embodiment, the shroud 222 may be attached to the deflector plate 218 by welding, bonding, or any other attachment means. Raised members 226 may be positioned on the baffle 210 to assist in bursting bubbles that form as liquid enters the canister. The raised members 226 may be spikes such as those shown in FIGS. 2, 5, 6, and 7B, or alternatively, the raised members 226 may be ridges, ribs, cleats, domes, projections, or any other structure that is capable of bursting a bubble. Additionally or alternatively, the deflector plate 218 may also include a surfactant coating to reduce the surface energy of the bubbles.

Figure 6:
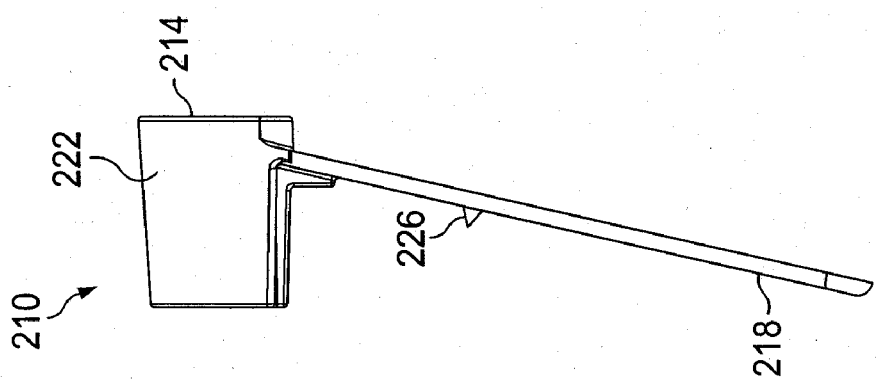
FIG. 6 depicts a front view of the baffle of FIG. 2.
Figure 5:
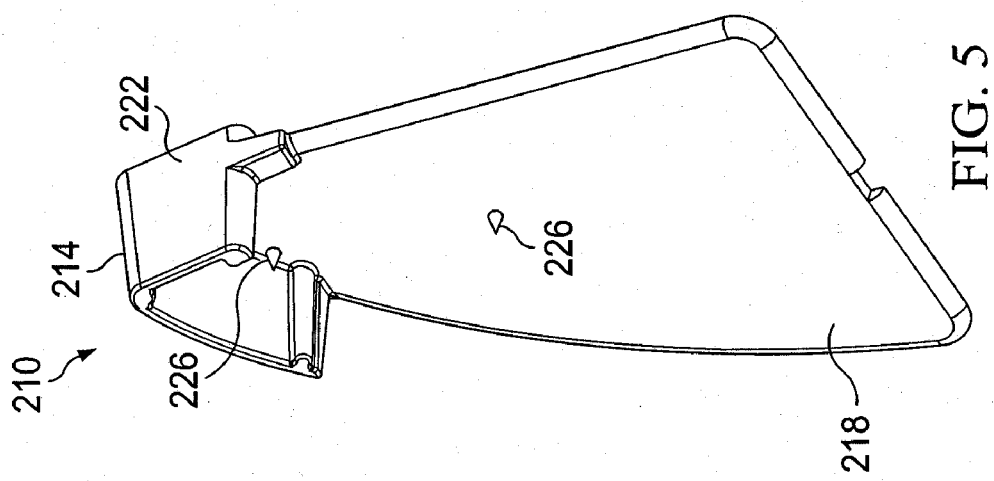
FIG. 5 illustrates a front perspective view of the baffle of FIG. 2.
Figure 7A:
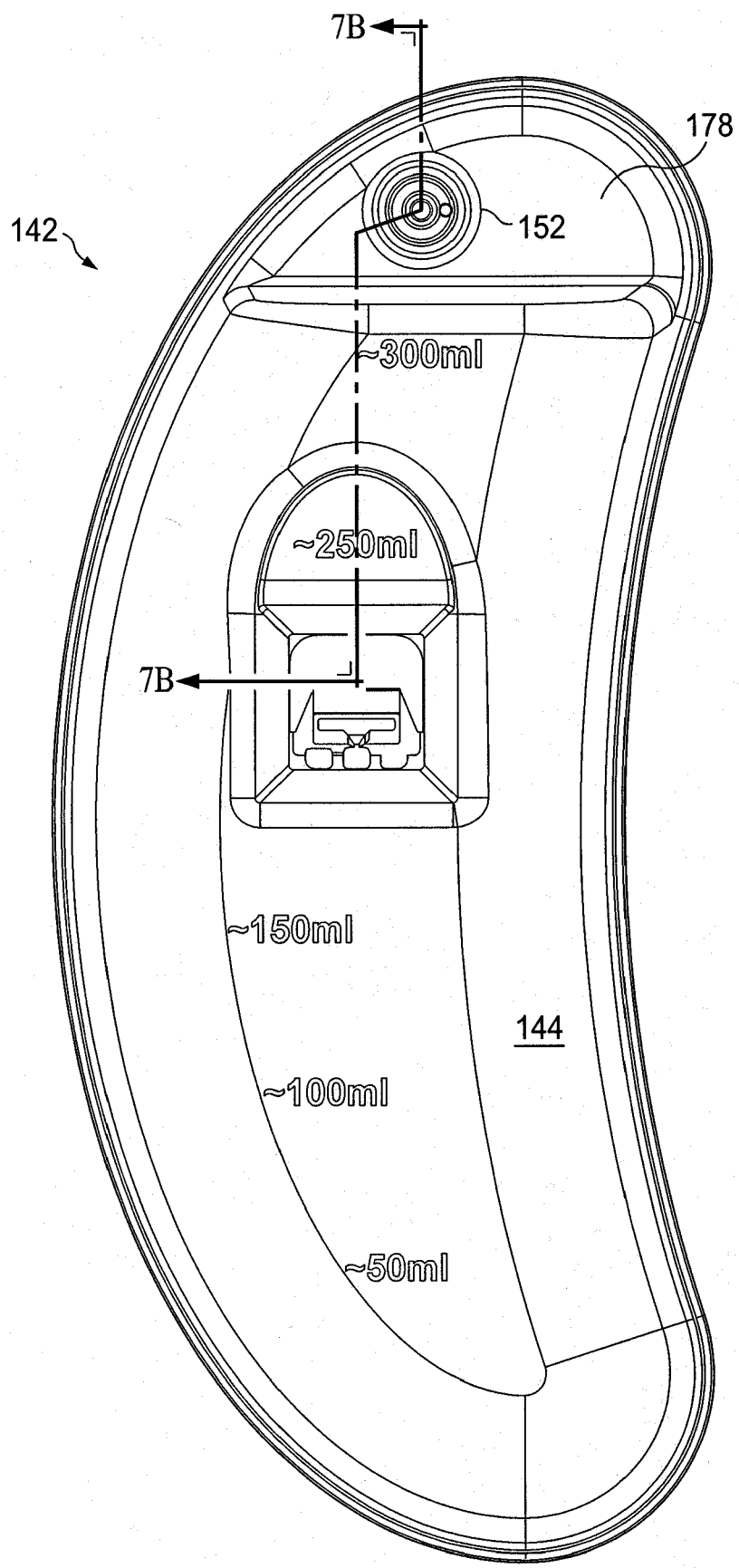
FIG. 7A illustrates a top view of the canister of FIG. 2.

While the deflector plate 218 illustrated in FIGS. 5 and 6 is substantially solid, the deflection plate 218 and other components of the baffle 210 may include holes, slots, channels, or other apertures. These apertures may facilitate improved gas transmission but still provide the blocking or deflecting characteristics necessary to minimize or prevent protein deposition on the liquid-air separator. In one illustrative embodiment, the baffle may be a screen or may be constructed from a screen material. In another embodiment, the baffle may include a deflector plate or other components that are permeable or semi-permeable to gas flow.

When assembled, the base 214 of the baffle 210 is removably received by the open end 172 of the entry chamber 170. As illustrated in FIGS. 6 and 7B, the deflector plate 218 may be angled relative to the base 214 such that fluid entering the entry chamber and striking the deflector plate is directed away from the exit wall 148. When the baffle 210 is installed in canister 142, the deflector plate may be angled relative to a level-liquid line of the canister. The level-liquid line is a line or plane represented by a top surface of liquid collecting in the canister 142 when the canister is oriented in a substantially upright position.

Referring more specifically to FIG. 7, the path of fluid entering the canister 142 is schematically depicted by line 234. The fluid passes through the inlet 152 and into the entry chamber 170. The fluid then passes beneath the shroud of the baffle 210 and is directed downward by the deflector plate 218 through the aperture 190 and open end 172 of the entry chamber 170. As the fluid enters the collection chamber 166, liquid in the fluid stream is pulled downward by gravity to collect in the bottom of the collection chamber 166. Gases in the fluid stream may be pulled upward around the deflector plate 218 to exit the canister 142 at the outlet 156.

The baffle 210 creates a tortuous pathway (as illustrated, for example, by line 234) for fluid entering and traveling through the canister 142. This tortuous pathway reduces and substantially prevents premature blocking of the liquid-air separator 160 by liquid entering the canister 142. Additionally, the deflector plate 218 of the baffle 210, and optionally the raised members 226, serve to prevent protein bubbles in the liquid exudate from forming or to block bubbles that have formed from reaching the liquid-air separator 160. The baffle 210 also serves to prevent or substantially reduce line-of-sight between the open end 172 of the entry chamber 170 and the liquid-air separator 160.

When installed in the canister 142, the baffle 210 is positioned to receive droplets or spray from bubbles bursting within the canister. In some cases, the baffle 210 may be positioned between the outlet 156 of the canister 142 and an area of the canister where exudate bubbles burst, i.e. a bubble-bursting area. In some cases, the baffle 210 may be positioned between the outlet 156 and a droplet-formation area. The droplet-formation area is the location at which exudate droplets from bursting bubbles are formed or land. In some embodiments, the bubble-bursting area and droplet-formation area of a canister may be at the same location or near one another. In other embodiments, the bubble-bursting area and droplet-formation area may be at different locations. For the canister 142 illustrated in FIGS. 1-6, 7A and 7B, the bubble-bursting area and droplet-formation area are within the entry chamber 170 or near the open end 172 and aperture 190 of the entry chamber 170.

It should be noted that other means exist for creating a tortuous pathway for fluid entering the canister 142. In one embodiment, a porous, reticulated foam such as a polyurethane foam may be positioned within the entry chamber 170. The reticulated nature of the foam minimizes bubble formation near the open end 172 of the entry chamber 170, which limits protein deposition on the liquid-air separator 160. Similarly, other foams or materials may be placed within the entry chamber 170 or between the entry chamber 170 and the liquid-air separator 160 to prevent premature blocking of the liquid-air separator 160. In canisters that may not include a separate entry chamber, a porous foam may be placed anywhere in the canister to prevent protein deposition on the liquid-air separator. Preferably, the positioning of the porous foam in the canister is such that the foam is located between a droplet-formation area or bubble-bursting area and the outlet of the canister.

Figure 8:
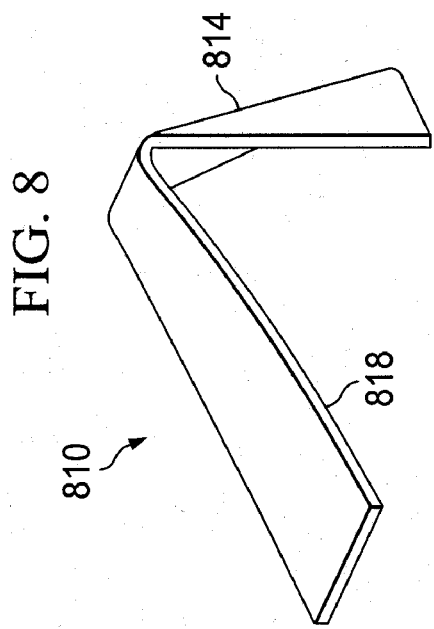
FIG. 8 illustrates a baffle according to an illustrative embodiment.

Referring to FIG. 8, a baffle 810 according to an illustrative embodiment is illustrated. Similar to the baffle 210, the baffle 810 also includes a base 814 and a deflector plate 818, but the baffle 810 is manufactured with a thermo-stamping process. The baffle 810 may be used with a canister similar to canister 142 or may be used other canisters. Baffle 810 also operates by blocking line-of-sight and creating a tortuous pathway between an outlet of a canister and at least one of an inlet, a bubble-bursting area, a droplet-formation area, and an open end of an entry chamber. In this way, the baffle 810 is capable of preventing premature blocking of a liquid-air separator associated with the outlet of the canister.

A method for collecting exudate from a tissue site is further provided according to an illustrative embodiment. The method includes creating a reduced pressure within a collection canister to draw exudate from the tissue site to the collection canister. The collection canister includes an outlet and a liquid-air separator associated with the outlet. The method further includes minimizing or preventing the deposition of protein from the exudate on the liquid-air separator. Minimization or prevention of protein deposition may occur in several different ways, including by providing a baffle or porous foam as described previously herein. In this way, exudate entering the canister may be deflected away from the liquid-air separator. Protein deposition may further be minimized or prevented by preventing or substantially reducing line-of-sight between a bubble-bursting area of the collection canister and the outlet. Alternatively or additionally, a tortuous path may be created for exudate entering the collection canister.

Certain embodiments of the illustrative embodiments described herein may also include means to reduce the likelihood of bubble formation, such as a fluid inlet transition from conduit to canister body. This fluid inlet transition may be designed with fluid flow characteristics that minimize cavitations and bubble formation. Additionally or alternatively, some embodiments may also include a surface coating of the liquid-air separator, such as an oliophobic coating, that minimizes protein deposition when exposed to protein bubbles.

It will be appreciated that the illustrative embodiments described herein may be used with reduced pressure treatment systems of any type, shape, or size and similarly with canisters of any type, shape, or size. The location of the inlet, outlet, and liquid-air separator may also vary depending upon the particular canister design. Similarly, the geometry of the baffle may be modified as necessary to conform to the contours or configuration of the canister. It should also be noted that the baffle is not limited to use with a reduced pressure treatment system. The baffle may also be used with other medical collection canisters that may benefit from a device that prevents premature blocking of a liquid-air separator.

It should be apparent from the foregoing that an invention having significant advantages has been provided. While the invention is shown in only a few of its forms, it is not just limited but is susceptible to various changes and modifications without departing from the spirit thereof.

We claim:

1. A reduced pressure treatment system comprising:
   a manifold positioned at a tissue site;
   a canister having a collection chamber, an inlet, and an outlet, the inlet being fluidly connected to the porous pad;
   a reduced pressure source fluidly connected to the outlet of the canister to deliver a reduced pressure to the collection chamber and the tissue site such that fluid from the tissue site is drawn into the collection chamber;
   a liquid-air separator associated with the outlet to prevent liquid from exiting the collection chamber through the outlet;
   a baffle positioned within the canister to deflect liquid entering the canister from prematurely blocking the liquid-air separator;
   wherein the baffle includes a deflector plate;
   wherein at least one raised member is positioned on the deflector plate to burst bubbles that form as fluid enters the collection chamber.

2. The system of claim 1, wherein the baffle creates a tortuous path between the inlet and the outlet.

3. The system of claim 1, wherein the baffle prevents line-of-sight between a droplet-formation area and the outlet of the canister.

4. The system of claim 1, wherein the baffle is a screen.

5. The system of claim 1, wherein the baffle includes a deflector plate that extends below the liquid-air separator.

6. The system of claim 1, wherein the outlet and the liquid-air separator are positioned on an exit wall of the collection chamber.

7. The system of claim 6, wherein the baffle includes a deflector plate that is angled, when positioned within the canister, relative to a level-liquid line of the canister to direct fluid contacting the deflector plate away from the exit wall.

8. The system of claim 1, wherein the liquid-air separator is a hydrophobic filter.

9. A collection canister for use with a reduced pressure treatment system, the canister comprising:
   a collection chamber;
   an inlet adapted to be fluidly connected to a tissue site;
   an outlet adapted to be fluidly connected to a reduced pressure source;
   a liquid-air separator positioned adjacent the outlet; and a baffle positioned within the canister to deflect liquid entering the canister from prematurely blocking the liquid-air separator;

wherein the baffle includes a deflector plate;

wherein at least one raised member is positioned on the deflector plate to burst bubbles that form as fluid enters the collection chamber.

10. The collection canister of claim 9, wherein the baffle creates a tortuous path between the inlet and the outlet.

11. The collection canister of claim 9, wherein the baffle prevents line-of-sight between a bubble-bursting area and the outlet of the canister.

12. The collection canister of claim 9, wherein the baffle is a screen.

13. The collection canister of claim 9, wherein the baffle includes a deflector plate that extends below the liquid-air separator.

14. The collection canister of claim 9, wherein the outlet and the liquid-air separator are positioned on an exit wall of the collection chamber.

15. The collection canister of claim 14, wherein the baffle includes a deflector plate that is angled, when positioned within the canister, relative to a level-liquid line of the canister to direct fluid contacting the deflector plate away from the exit wall.

16. A collection canister for use with a reduced pressure treatment system, the canister comprising:

a collection chamber;

an entry chamber positioned above the collection chamber, the entry chamber having an open end and a closed end defined by an entry wall, the entry chamber further having a floor separating the entry chamber from the collection chamber, the floor having an aperture allowing communication between the entry chamber and the collection chamber;

an inlet disposed in the entry wall of the entry chamber, the inlet adapted to be fluidly connected to a tissue site;

an outlet in communication with the collection chamber and adapted to be fluidly connected to a reduced pressure source;

a hydrophobic filter positioned adjacent the outlet to prevent liquid from exiting the collection chamber through the outlet; and a baffle having a base and a deflector plate, the base being removably positioned within the entry chamber through the opening of the entry chamber;

wherein the deflector plate of the baffle deflects liquid entering the entry chamber through the inlet from prematurely blocking the hydrophobic filter;

wherein at least one raised member is positioned on the deflector plate to burst bubbles that form as fluid enters the collection chamber.

17. The collection canister of claim 16, wherein the baffle creates a tortuous pathway between the entry chamber and the outlet of the canister.

18. The collection canister of claim 16, wherein the baffle prevents line-of-sight between the opening of the entry chamber and the outlet of the canister.

19. The collection canister of claim 16, wherein the baffle is a screen.

20. The collection canister of claim 16, wherein the deflector plate extends below the hydrophobic filter.

21. The collection canister of claim 16, wherein the outlet and the hydrophobic filter are positioned on an exit wall of the collection chamber opposite the entry wall of the entry chamber.

22. The collection canister of claim 21, wherein the deflector plate is angled relative to the base to direct fluid contacting the deflector plate away from the exit wall.

23. The collection canister of claim 21, wherein the outlet and the hydrophobic filter are positioned below the floor of the entry chamber.

24. The collection canister of claim 16, wherein the aperture is a slot.

25. The collection canister of claim 16, wherein:

the baffle prevents line-of-sight between the opening of the entry chamber and the outlet of the canister;

the outlet and the hydrophobic filter are positioned on an exit wall of the collection chamber opposite the entry wall of the entry chamber and below the floor of the entry chamber; and the deflector plate extends below the hydrophobic filter.

26. A collection canister for use with a reduced pressure treatment system, the canister comprising:

a collection chamber;

an inlet adapted to be fluidly connected to a tissue site;

an outlet adapted to be fluidly connected to a reduced pressure source;

a liquid-air separator positioned adjacent the outlet; and a baffle positioned within the canister to receive droplets or spray from bubbles bursting within the canister;

wherein the baffle includes a deflector plate;

wherein at least one raised member is positioned on the deflector plate to burst bubbles that form as fluid enters the collection chamber.

27. The collection canister of claim 26, wherein the baffle is positioned between a droplet-formation area and the outlet.

28. The collection canister of claim 26, wherein:

the bubbles burst in a droplet-formation area of the canister; and the baffle is positioned between the droplet-formation area and the outlet.

29. A method for collecting exudate from a tissue site comprising:

creating a reduced pressure within a collection canister to draw exudate from the tissue site to the collection canister, the collection canister having an outlet and a liquid-air separator associated with the outlet; and minimizing deposition of protein from the exudate on the liquid-air separator;

wherein said minimizing said deposition of protein further comprises:

providing a baffle within the collection canister to deflect exudate entering the canister;

wherein the baffle includes a deflector plate;

wherein at least one raised member is positioned on the deflector plate to burst bubbles that form as exudate enters the collection chamber.

30. The method of claim 29, wherein minimizing deposition further comprises preventing deposition.

31. The method of claim 29, wherein minimizing deposition further comprises:

preventing line-of-sight between a bubble-bursting area of the collection canister and the outlet.

32. The method of claim 29, wherein minimizing deposition further comprises:

creating a tortuous path for exudate entering the collection canister.

* * * * *